(12) United States Patent
Petrick et al.

(10) Patent No.: US 7,763,012 B2
(45) Date of Patent: Jul. 27, 2010

(54) DEVICES AND METHODS FOR CROSSING A CHRONIC TOTAL OCCLUSION

(75) Inventors: Timothy B. Petrick, Brooklyn Park, MN (US); Steven N. Willard, Brooklyn Center, MN (US); Peter T. Keith, St. Paul, MN (US); Dennis W. Wahr, Minnetonka, MI (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1559 days.

(21) Appl. No.: 10/653,879

(22) Filed: Sep. 2, 2003

(65) Prior Publication Data

US 2005/0049574 A1    Mar. 3, 2005

(51) Int. Cl.
*A61M 25/00* (2006.01)
*A61M 37/00* (2006.01)

(52) U.S. Cl. .................. 604/527; 604/525; 604/103.09
(58) Field of Classification Search ................. 604/525, 604/103.09; 600/433; 433/18, 19, 22
See application file for complete search history.

(56) References Cited

U.S. PATENT DOCUMENTS

| | | | |
|---|---|---|---|
| 2,688,329 A | 9/1954 | Wallace | |
| 4,723,936 A | 2/1988 | Buchbinder | |
| 4,757,827 A | 7/1988 | Buchbinder | |
| 4,793,359 A | 12/1988 | Sharrow | |
| 4,838,268 A | 6/1989 | Keith | |
| 4,898,577 A | 2/1990 | Badger | |
| 4,932,419 A | 6/1990 | De Toledo | |
| 4,951,677 A | 8/1990 | Crowley et al. | |
| 4,960,411 A | 10/1990 | Buchbinder | |
| 4,983,165 A | 1/1991 | Loiterman | |
| 4,998,923 A | 3/1991 | Samson | |
| 5,002,041 A | 3/1991 | Chikama | |
| 5,030,204 A | 7/1991 | Badger | |
| 5,037,391 A | 8/1991 | Hammerslag | |
| 5,060,660 A | 10/1991 | Gambale | |
| 5,102,390 A | 4/1992 | Crittenden | |
| 5,131,407 A | 7/1992 | Ischinger | |
| 5,154,705 A | 10/1992 | Fleischhacker | |

(Continued)

FOREIGN PATENT DOCUMENTS

EP    0 661 072    7/1995

(Continued)

*Primary Examiner*—Nicholas D Lucchesi
*Assistant Examiner*—Victoria P Campbell
(74) *Attorney, Agent, or Firm*—O'Melveny & Myers LLP

(57) ABSTRACT

A catheter comprises an elongate tubular member having a proximal end and a distal end, and a deflectable tip at the distal end of the elongate tubular member. The deflectable tip comprises a first helical coil having a first diameter and a second helical coil having a second diameter, the first diameter being larger than the second diameter. The first and second helical coils are arranged in the manner of a double helix. When viewed in cross-section, the first helical coil and the second helical coil are aligned at a first point on a circumference of each coil and misaligned at a second point on the circumference of each coil, where the second point is approximately 180 degrees from the first point. In certain embodiments the catheter further includes a dilatation balloon. Methods of use for crossing a chronic total occlusion are also described.

8 Claims, 11 Drawing Sheets

U.S. PATENT DOCUMENTS

| | | | |
|---|---|---|---|
| 5,158,548 | A | 10/1992 | Lau |
| 5,165,421 | A | 11/1992 | Fleischhacker |
| 5,228,441 | A | 7/1993 | Lundquist |
| 5,269,757 | A | 12/1993 | Fagan |
| 5,279,561 | A | 1/1994 | Roucher |
| 5,290,247 | A | 3/1994 | Crittenden |
| 5,315,996 | A | 5/1994 | Lundquist |
| 5,358,493 | A * | 10/1994 | Schweich et al. ............ 604/264 |
| 5,373,619 | A | 12/1994 | Fleischhacker |
| 5,449,343 | A | 9/1995 | Samson |
| 5,477,856 | A | 12/1995 | Lundquist |
| 5,484,407 | A | 1/1996 | Osypka |
| 5,628,761 | A | 5/1997 | Rizik |
| 5,678,296 | A | 10/1997 | Fleischhacker |
| 5,700,253 | A | 12/1997 | Parker |
| 5,916,193 | A | 6/1999 | Stevens |
| 5,935,108 | A | 8/1999 | Katoh et al. |
| 5,984,945 | A | 11/1999 | Sirhan |
| 6,068,623 | A | 5/2000 | Zadno-Azizi et al. |
| 6,110,164 | A | 8/2000 | Vidlund |
| 6,152,912 | A | 11/2000 | Jansen et al. |
| 6,156,046 | A | 12/2000 | Passafaro et al. |
| 6,190,332 | B1 | 2/2001 | Muni et al. |
| 6,210,395 | B1 | 4/2001 | Fleischhacker |
| 6,210,408 | B1 | 4/2001 | Chandrasekaran et al. |
| 6,302,893 | B1 | 10/2001 | Limon |
| 6,355,016 | B1 | 3/2002 | Bagaoisan et al. |
| 6,375,628 | B1 | 4/2002 | Zadno-Azizi et al. |
| 6,375,629 | B1 | 4/2002 | Muni et al. |
| 6,394,976 | B1 | 5/2002 | Winston et al. |
| 6,468,230 | B2 | 10/2002 | Muni et al. |
| 6,482,221 | B1 | 11/2002 | Hebert |
| 6,569,129 | B1 | 5/2003 | Holmes |
| 6,623,448 | B2 | 9/2003 | Slater |
| 2001/0016705 | A1 | 8/2001 | Omaleki et al. |
| 2001/0021831 | A1* | 9/2001 | Fleischhacker et al. ..... 604/264 |
| 2001/0044591 | A1 | 11/2001 | Stevens |
| 2002/0010420 | A1 | 1/2002 | Bagaoisan et al. |
| 2002/0077595 | A1* | 6/2002 | Hundertmark et al. . 604/103.09 |
| 2002/0095137 | A1 | 7/2002 | Zadno-Azizi et al. |
| 2003/0004460 | A1 | 1/2003 | Bedell |
| 2003/0023261 | A1 | 1/2003 | Tomaschko et al. |
| 2003/0105426 | A1* | 6/2003 | Jorgensen ................ 604/103.1 |

FOREIGN PATENT DOCUMENTS

| | | |
|---|---|---|
| WO | WO 97/44084 | 11/1997 |
| WO | WO 98/39048 | 9/1998 |
| WO | WO 98/56448 | 12/1998 |
| WO | WO 99/42158 | 8/1999 |
| WO | WO 01/78825 | 10/2001 |

* cited by examiner

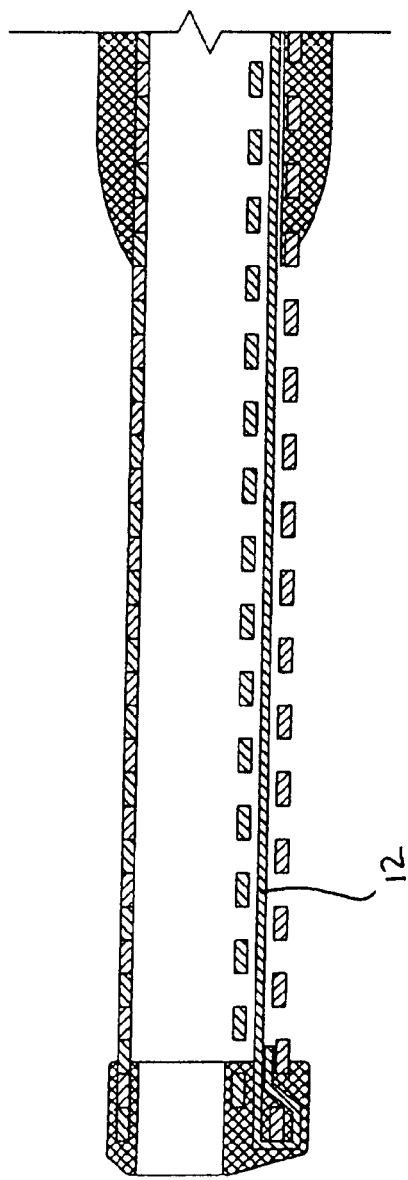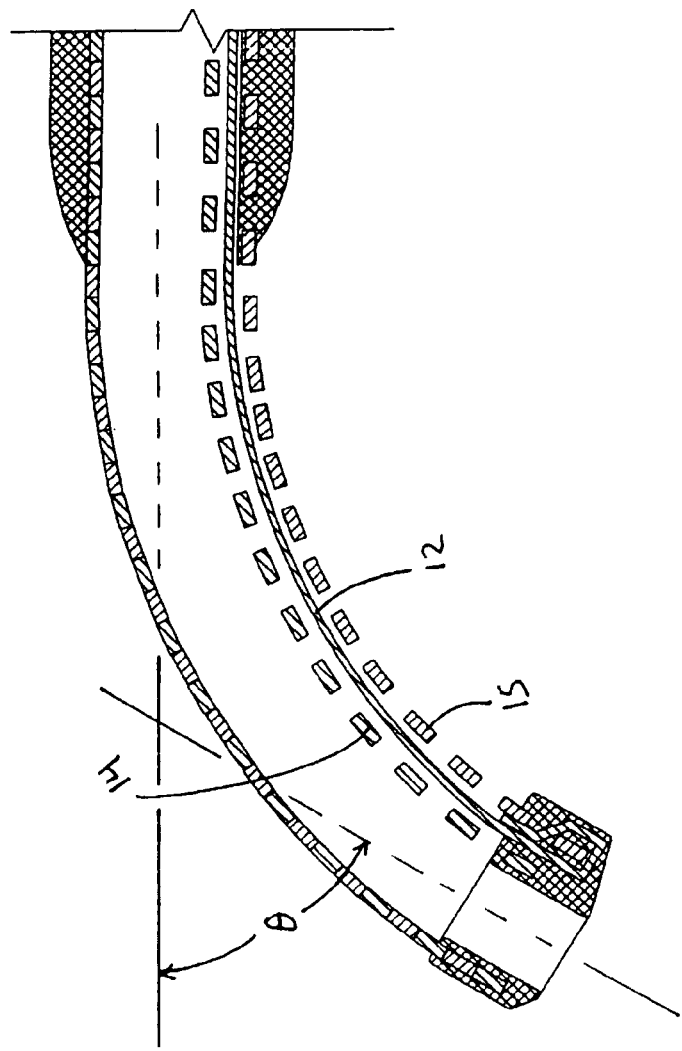

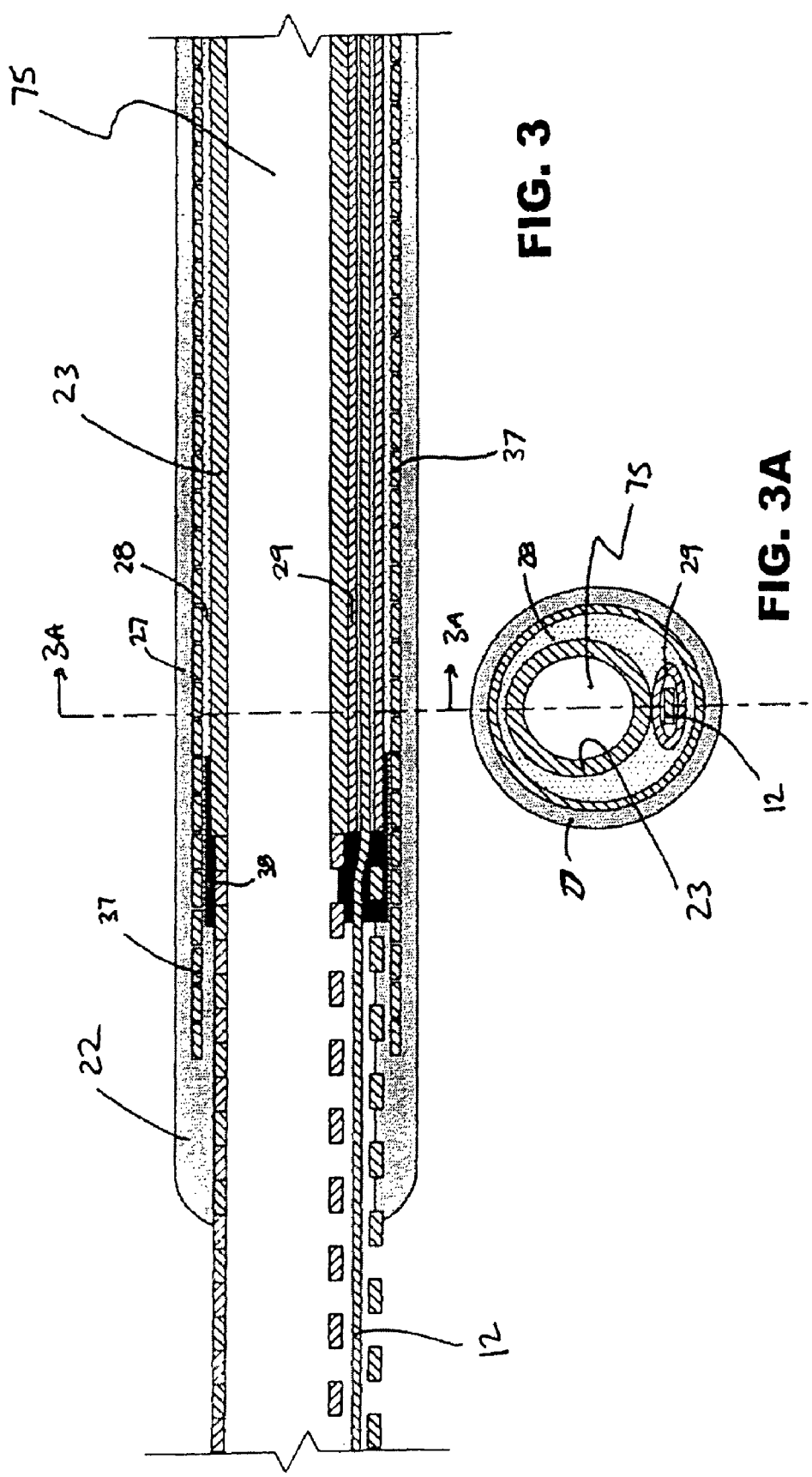

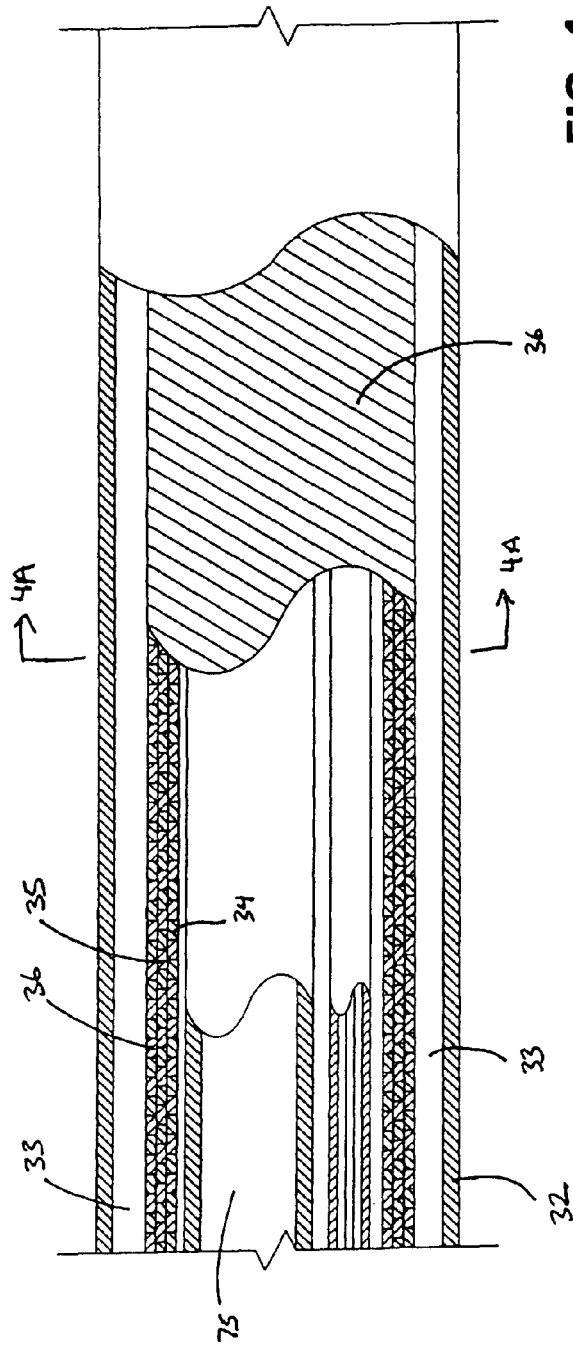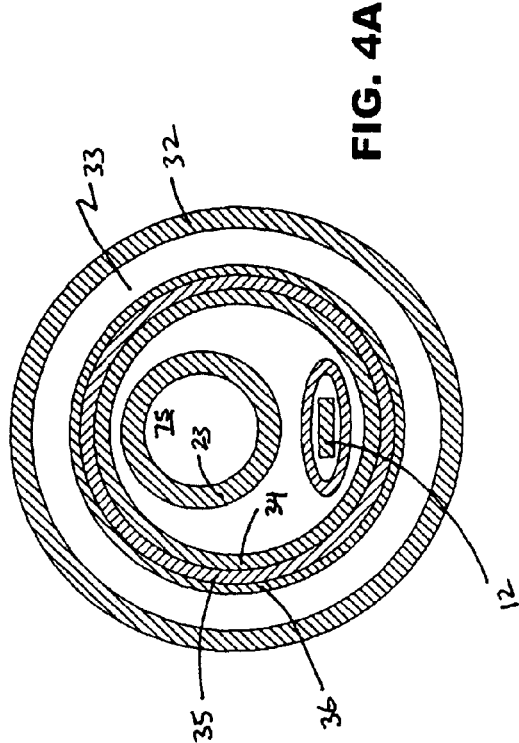

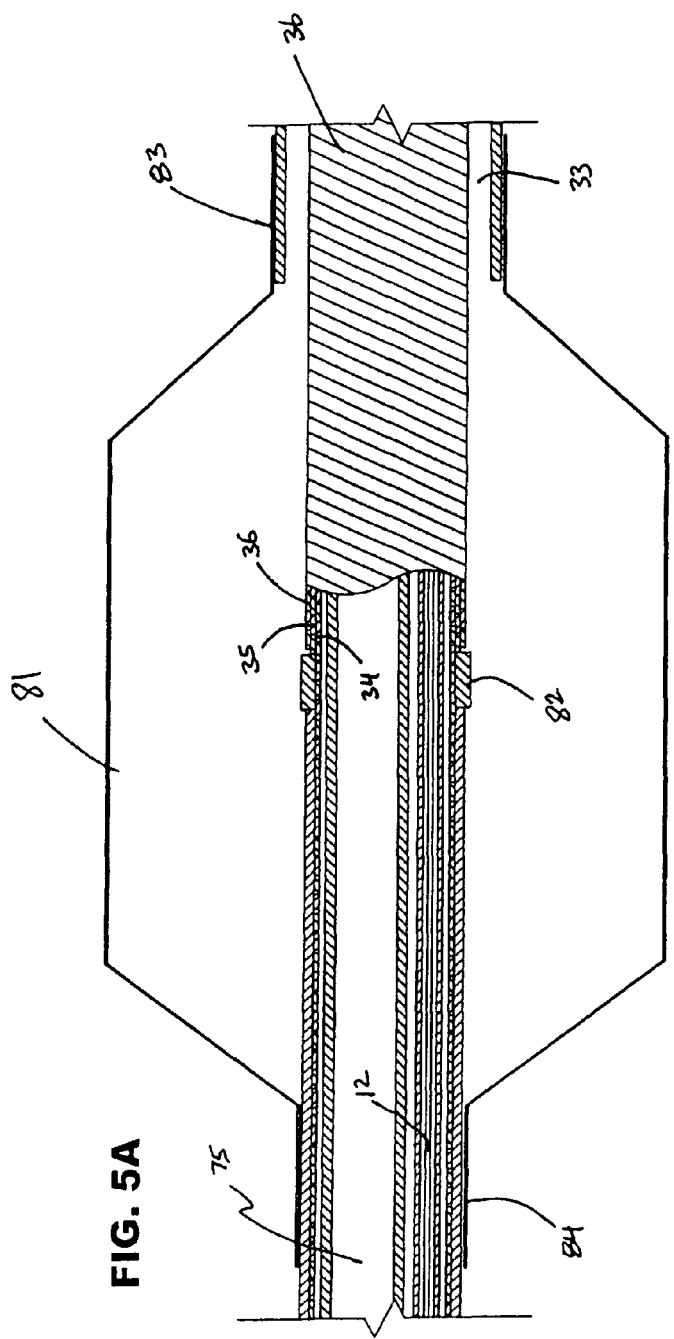
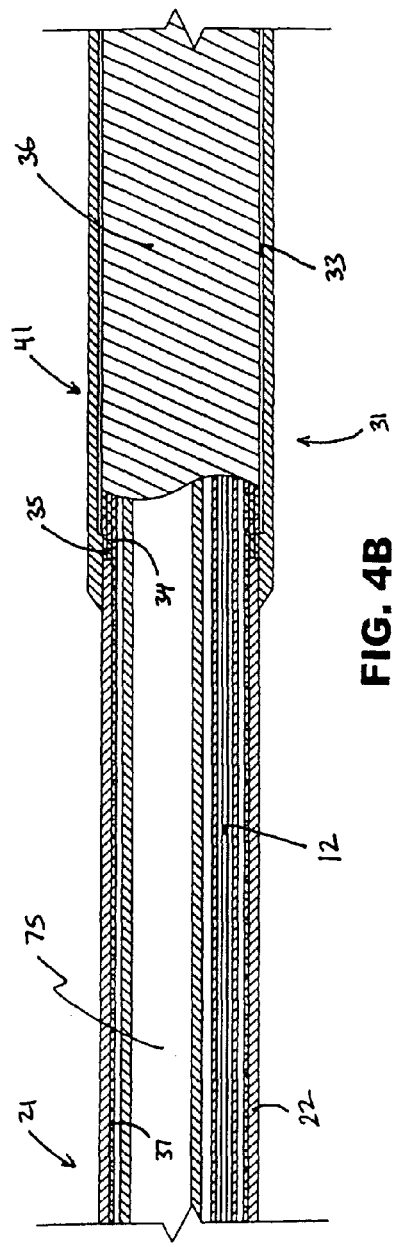
FIG. 5A
FIG. 4B

DEVICES AND METHODS FOR CROSSING A CHRONIC TOTAL OCCLUSION

FIELD OF THE INVENTION

The present invention relates to apparatus and methods used to cross lesions in blood vessels, and in more particular embodiments, catheters for controlling a guidewire to cross a chronic total occlusion in a blood vessel.

BACKGROUND

Chronic Total Occlusions (CTOs) are vascular lesions which are totally occluded and thereby inhibit normal blood flow. Such occlusions can occur anywhere in a patient's vascular system, arteries, and veins, including coronary vessels, as well as carotid arteries, renal arteries, cerebral arteries, arteries of the head and neck, iliac arteries, femoral arteries, popliteal arteries, and other peripheral arteries.

Typically, a CTO may be occluded for several weeks to several months, or longer. Such blockages can have serious medical consequences, depending upon their location within a patient's vascular system. For example, blockage of the coronary vessels that supply blood to the heart can cause damage to the heart.

Since most lesions form episodically over a long period of time, the ischemic tissue distal the lesion has time to form collateral circulation. In the case of coronary arteries, these collateral vessels can form from the proximal artery and connect into the distal artery ("ipsilateral collaterals") or can form from the other major arterial branches and connect into the distal artery ("contralateral collaterals"). When the lesion finally becomes a total occlusion, the collateral circulation is typically sufficient to keep the distal tissue alive, though ischemic. In cardiac circulation, this ischemic tissue causes angina. Therefore, it is desirable to reestablish flow to the distal tissue.

Various surgical procedures are currently used to reestablish flow through or around the blockage in blood vessels. Such procedures include coronary artery bypass graft surgery and balloon angioplasty. Balloon angioplasty typically involves inserting a balloon catheter over a guidewire and into the occlusive lesion, expanding the balloon in the lesion, and if necessary, placing a stent in the now expanded lesion to keep it open.

Chronic total occlusions are more difficult to cross than partially occluded lesions because a guidewire must penetrate the lesion, rather than navigate a pre-existing lumen. Complications may result from these difficulties. For example, the distal end and tip of the guidewire may have insufficient support or rigidity to enter the lesion, causing the end to buckle. Or the guidewire may perforate the vessel, especially when the distal end and tip of the guidewire is not oriented towards the occlusion. If the guidewire has a pre-formed bend at the tip to assist in its initial orientation as it enters the occlusion, the internal lesion tissue may cause the guidewire to take an unwanted path within the occlusion. If the guidewire cannot successfully cross the occlusion, subsequent therapeutic devices, such as a balloon angioplasty catheter, cannot be advanced across the occlusion to dilate and treat it. Similar problems are encountered when attempting to cross an occlusion at a bifurcation. A guidewire having insufficient support or rigidity to enter the lesion will bend or, in some cases, perforate the vessel at the bifurcation.

For these reasons, the success rate for crossing and treating CTOs is much lower than that for partially occluded lesions, particularly for coronary CTOs. Furthermore, even when the total occlusion is successfully crossed with conventional guidewires, it often requires a great deal of time and skill on the part of the physician. Thus, there is a need for an improved system and method of crossing an occlusion.

SUMMARY OF THE INVENTION

The present invention relates to a catheter comprising an elongate tubular member having a proximal end and a distal end, and a deflectable tip at the distal end of the elongate tubular member. In one embodiment, the deflectable tip may comprise a first helical coil having a first diameter and a second helical coil having a second diameter, the first diameter being larger than the second diameter. The first and second helical coils are arranged in the manner of a double helix. When viewed in cross-section, the first helical coil and the second helical coil are aligned at a first point on a circumference of each coil and misaligned at a second point on the circumference of each coil, where the second point is approximately 180 degrees from the first point. In certain cases the first helical coil and the second helical coil are bonded at one or more points of alignment of the double helix.

The catheter further includes a control wire operable from the proximal end of the catheter and extending to the distal end of the catheter where the control wire is secured at a distal region of the deflectable tip. The control wire extends through the deflectable tip and may be disposed within the eccentric annulus between the first helical coil and the second helical coil within the circumferential region where the first helical coil and the second helical coil are misaligned. The control wire may be a metallic wire, a polymeric thread, or any other suitable material.

The catheter may further include a lumen extending between the proximal and the distal ends of the elongate tubular member. The lumen is adapted to slideably receive a guidewire. One or more radiopaque markers may be attached to a distal region of the catheter to mark the location of the catheter when in use. In other embodiments, the catheter further includes a dilatation balloon that communicates with an inflation lumen that extends to the proximal end of the catheter.

In use, the physician provides a catheter having an elongate tubular member with a proximal end and a distal end, and a deflectable tip at the distal end of the catheter as described above. The catheter is advanced to a region of interest in an artery proximal a lesion. The control wire is operated to direct the deflectable tip toward the lesion. A guidewire is advanced through the lumen of the catheter and into the lesion to cross the lesion.

Once the lesion has been accessed in this manner, a dilatation balloon can be used to dilate the lesion. In one embodiment, the catheter of the present invention carries the dilatation balloon. The catheter is advanced over the guidewire to cross the lesion and the balloon is expanded to dilate the lesion. In another embodiment, the catheter is then removed from the region of interest while the guidewire is maintained across the lesion. An angioplasty catheter is then advanced across the lesion, and the lesion is dilated. In a further alternative embodiment, the catheter is removed from the region of interest while the guidewire is maintained across the lesion. A stent catheter is then advanced across the lesion, and the lesion is dilated with a stent.

It is contemplated that the invention will find use anywhere in the human vasculature, including in the coronary arteries, including the left anterior descending, the left circumflex, the right coronary artery, the obtuse marginal, and the left main coronary artery, as well as in the carotid arteries.

In another embodiment, the catheter comprises an elongate tubular member having a proximal region, a distal region, and a lumen extending therebetween. A multilayer torque cable is disposed in the proximal region of the elongate tubular member. The multilayer torque cable includes a first helical coil and a second helical coil. The first helical coil is nested within the second helical coil and wound in a reverse direction from the second helical coil. Rotation of the first helical coil in a first direction causes the first helical coil to expand while rotation of the second helical coil in the first direction causes the second helical coil to compress and thereby interfere with the expansion of the first helical coil. A third helical coil surrounding the second helical coil may be included in certain embodiments. The catheter further includes a monolayer helical coil in the distal region of the elongate tubular member. An outer jacket surrounds the monolayer helical coil to restrict expansion on rotation of the monolayer helical coil. Any one or more of the first helical coil, the second helical coil, the third helical coil, and the monolayer helical coil may be multifilar. Multifilar construction increases the pitch between coil windings, thereby increasing the tendency to expand on rotation, thereby maximizing the torque transmission properties.

In certain embodiments, a second outer jacket may be disposed about the multilayer torque cable. In the event that the catheter is a balloon catheter, a proximal end of the balloon may be bonded to the second outer jacket and a distal end of the balloon may be bonded to the outer jacket surrounding the monolayer helical coil.

In use, a catheter as described herein is provided to the physician. The catheter comprises an elongate tubular member having a proximal region, a distal region, and a lumen extending therebetween. The catheter further has a multilayer torque cable in the proximal region of the elongate tubular member as described above. The catheter further includes a monolayer helical coil in the distal region of the elongate tubular member and an outer jacket surrounding the monolayer helical coil to restrict expansion on rotation of the monolayer helical coil. The catheter is advanced to a region of interest e.g., in an artery proximal to a lesion.

The catheter may be further equipped with a deflectable tip at the distal end of the elongate tubular member. The deflectable tip may comprise a first helical coil having a first diameter and a second helical coil having a second diameter, the first diameter being larger than the second diameter. The first and second helical coils are arranged in the manner of a double helix. When viewed in cross-section, the first helical coil and the second helical coil are aligned at a first point on a circumference of each coil and misaligned at a second point on the circumference of each coil. The second point is approximately 180 degrees from the first point. The catheter is advanced to a region of interest in the artery proximal a lesion. The control wire is operated to direct the deflectable tip toward the lesion. Torque is applied to the proximal region of the catheter. The torque is transmitted through the multilayer torque cable in the proximal region of the elongate tubular member, and torque is transmitted through the monolayer helical coil in the distal region of the elongate tubular member. A guidewire is advanced through the lumen of the catheter and into the lesion to cross the lesion.

Once the lesion has been accessed in this manner, a dilatation balloon can be used to dilate the lesion. In one embodiment, the catheter of the present invention carries the dilatation balloon. The catheter is advanced over the guidewire to cross the lesion and the balloon is expanded to dilate the lesion. In another embodiment, the catheter is then removed from the region of interest while the guidewire is maintained across the lesion. An angioplasty catheter is then advanced across the lesion, and the lesion is dilated. In a further alternative embodiment, the catheter is removed from the region of interest while the guidewire is maintained across the lesion. A stent catheter is then advanced across the lesion, and the lesion is dilated with a stent.

As noted above, it is contemplated that the invention will find use anywhere in the human vasculature, including in the coronary arteries, including the left anterior descending, the left circumflex, the right coronary artery, the obtuse marginal, and the left main coronary artery, saphenous vein grafts as well as in the carotid arteries and other peripheral blood vessels.

In still another embodiment, a catheter is provided comprising a proximal handle, a torque cable extending distally from the proximal handle, and an outer jacket extending distally from the proximal handle. The outer jacket surrounds the torque cable with an annular gap disposed between the torque cable and the outer jacket. The annular gap allows the torque cable to rotate independently of the outer jacket for at least a portion of the length of the catheter.

The torque cable may be a multilayer torque cable comprising a first helical coil and a second helical coil. When this is the case, the first helical coil is nested within the second helical coil and wound in a reverse direction from the second helical coil. Rotation of the first helical coil in a first direction causes the first helical coil to expand while rotation of the second helical coil in the first direction causes the second helical coil to compress and thereby interfere with the expansion of the first helical coil, resulting in torsional stiffness. Any one or more of the first helical coil and the second helical coil may be multifilar. Multifilar construction increases the pitch between coil windings, thereby increasing the tendency to expand on rotation, thereby maximizing the torque transmission properties. The catheter may further include a balloon mounted on the distal region of the catheter, the balloon defining a chamber that communicates with the annular gap as an inflation lumen.

In use, a catheter as described above is provided to the physician. The catheter comprises a proximal handle, a torque cable extending distally from the proximal handle, and an outer jacket extending distally from the proximal handle and surrounding the torque cable. An annular gap is disposed between the torque cable and the outer jacket. The catheter is advanced to a region of interest in the artery proximal a lesion. Torque is applied to the proximal handle. The torque is transmitted through the torque cable with the outer jacket remaining stationary for at least a portion of its length. The annular gap allows the torque cable to rotate independently of the outer jacket.

The catheter may further include a deflectable tip at the distal end of the elongate tubular member. The deflectable tip comprises a first helical coil having a first diameter and a second helical coil having a second diameter, the first diameter being larger than the second diameter. The first and second helical coils are arranged in the manner of a double helix. When viewed in cross-section, the first helical coil and the second helical coil are aligned at a first point on a circumference of each coil and misaligned at a second point on the circumference of each coil. The second point is approximately 180 degrees from the first point.

The method further comprises the steps of advancing the catheter to a region of interest in the artery proximal a lesion. The control wire is operated to direct the deflectable tip toward the lesion. A guidewire is advanced through the lumen of the catheter and into the lesion to cross the lesion.

Once the lesion has been accessed in this manner, a dilatation balloon can be used to dilate the lesion. In one embodiment, the catheter of the present invention carries the dilatation balloon. The catheter is advanced over the guidewire to cross the lesion and the balloon is expanded to dilate the lesion. In another embodiment, the catheter is then removed from the region of interest while the guidewire is maintained across the lesion. An angioplasty catheter is then advanced across the lesion, and the lesion is dilated. In a further alternative embodiment, the catheter is removed from the region of interest while the guidewire is maintained across the lesion. A stent catheter is then advanced across the lesion, and the lesion is dilated with a stent.

As noted above, it is contemplated that the invention will find use anywhere in the human vasculature, including in the coronary arteries, including the left anterior descending, the left circumflex, the right coronary artery, the obtuse marginal, and the left main coronary artery, saphenous vein grafts as well as in the carotid arteries and other peripheral blood vessels.

BRIEF DESCRIPTION OF THE DRAWINGS

FIG. 2B shows a section view of the deflectable tip in a straight configuration.

FIG. 2C shows a section view of the deflectable tip in a curved configuration.

FIG. 3 depicts a section view of the tapered region of the catheter of FIG. 1.

FIG. 3A is a cross-section taken through section line 3A-3A in FIG. 3.

FIG. 4 depicts a partial section view of the mid-shaft section of the catheter of FIG. 1.

FIG. 4A is a cross-section taken through section line 4A-4A in FIG. 4.

FIG. 4B depicts the transition from the mid-shaft section to the tapered region of the catheter of FIG. 1.

FIG. 5A depicts the transition from the mid-shaft section to the tapered region of the catheter of FIG. 5.

DETAILED DESCRIPTION

Figure 1:
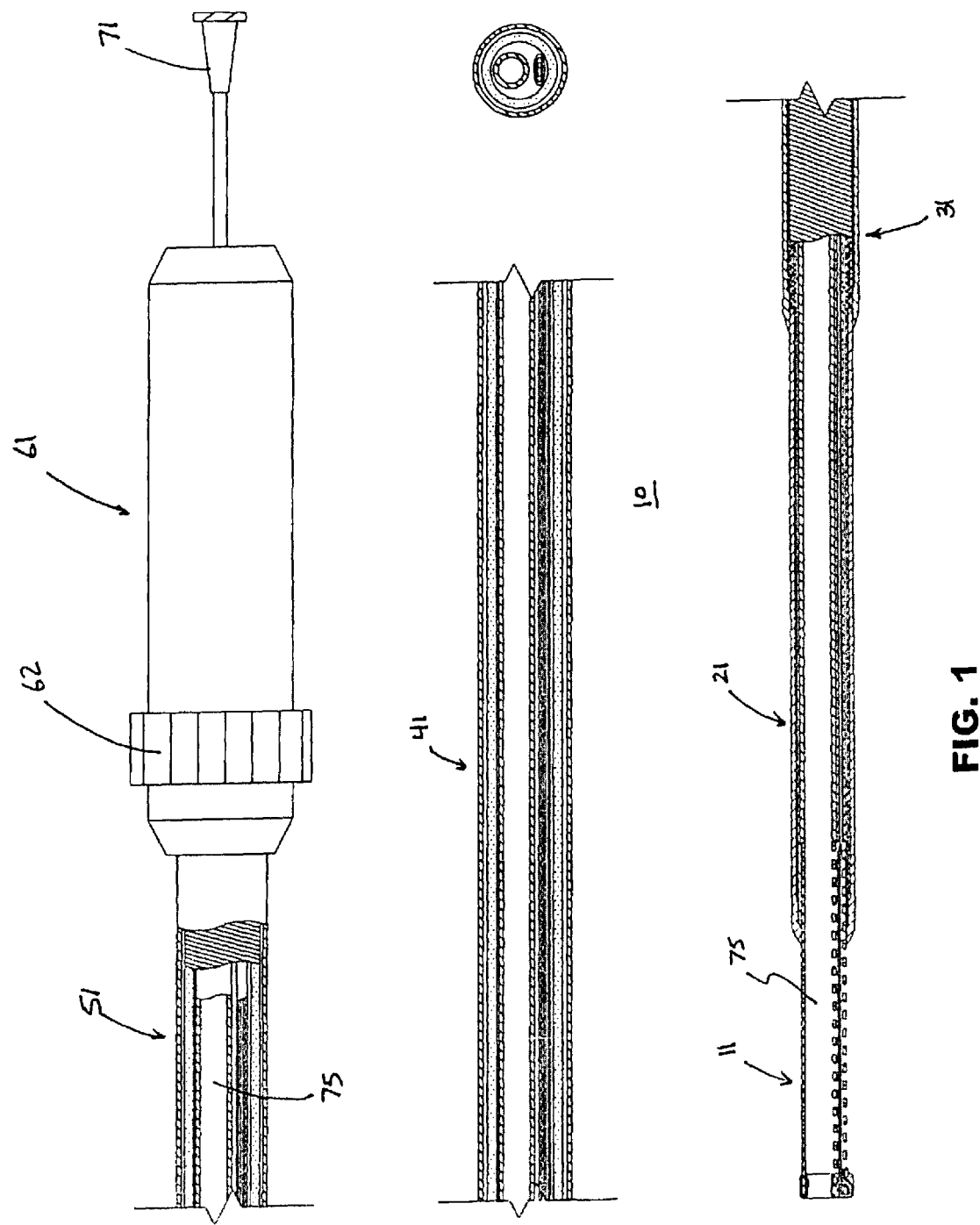
FIG. 1 depicts a partial section view of a catheter according to the present invention.

A first embodiment of articulating tip catheter 10 is illustrated in FIG. 1. This embodiment includes a variably deflectable tip region 11, a distal shaft region 21, a transition region 31, a main shaft region 41, a proximal shaft region 51, a handle 61, and lumen 75 communicating with luer 71.

Figure 2A:
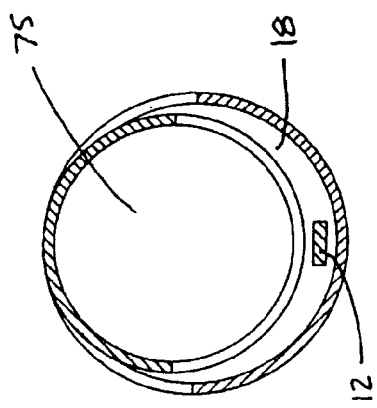
FIG. 2A is a cross-section taken through section line 2A-2A in FIG. 2.
Figure 2:
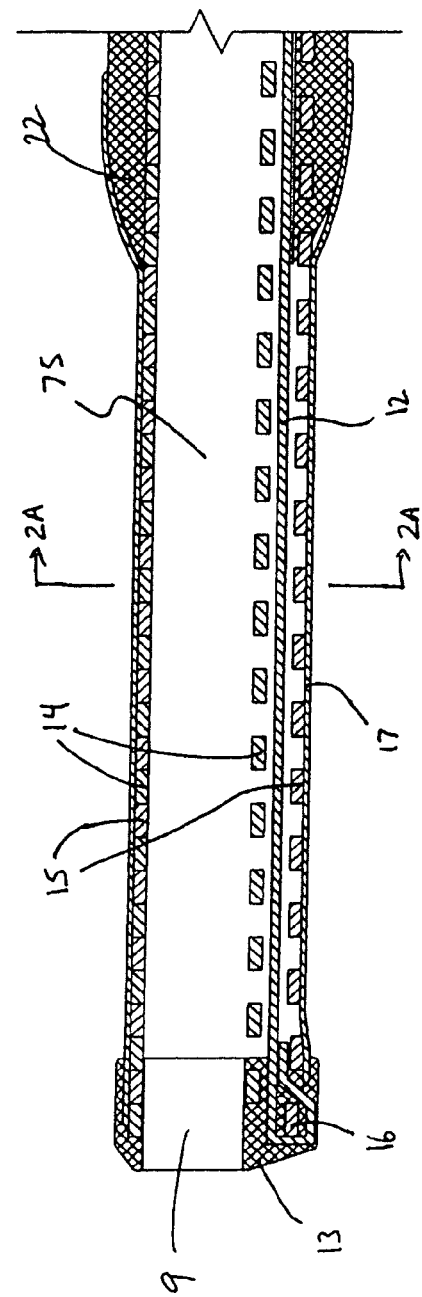
FIG. 2 depicts a section view of the deflectable tip of the catheter of FIG. 1.

FIG. 2 illustrates one embodiment of the deflectable tip region. An articulation structure is shown comprising two coils wound to two different diameters nested together, i.e., a smaller diameter inner coil 14, and a larger diameter outer coil 15. Control wire 12 is secured to distal end 13 of the articulation structure, by forming a loop in the control wire which surrounds the distal-most turn 16 of the outer coil. The control wire may be further secured to the coil structure by means of a spot weld. When the control wire is moved proximally relative to the catheter of FIG. 2B, the articulation structure is compressed longitudinally as shown in FIG. 2C. The nested coil structure is free to compress on the side adjacent the control wire (bottom of FIG. 2B). However, on the opposite side, where the coils are aligned, the structure is prevented from longitudinally compressing. Therefore, the nested coil structure deflects to form a deflection angle theta, shown in FIG. 2C. An articulation structure for a coronary type application can preferably deflect to a deflection angle of at least about 45 degrees, and more preferably about 90 degrees.

Figure 2D:
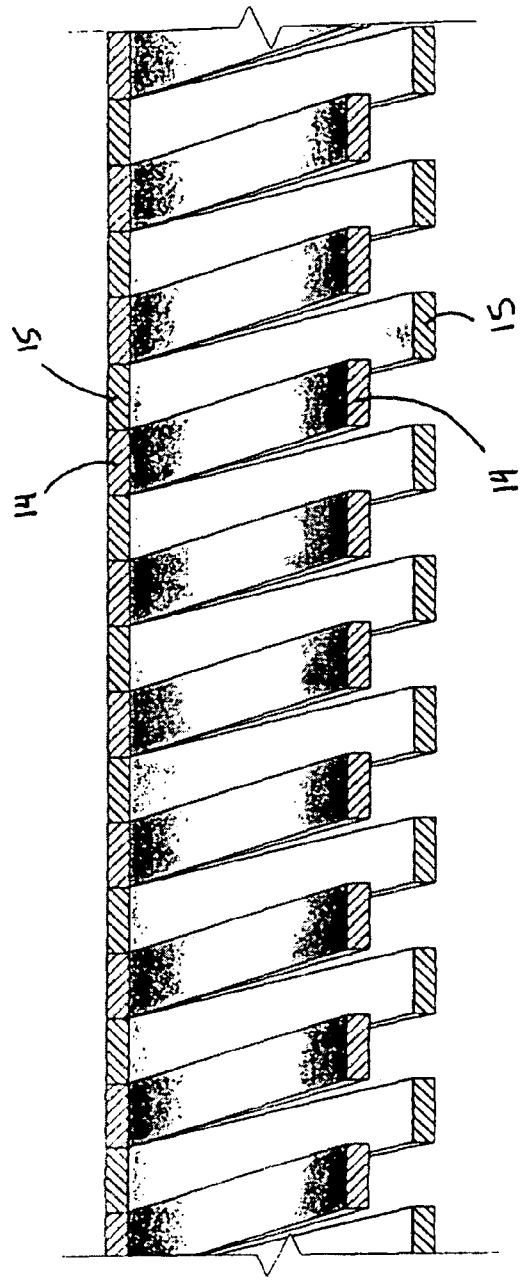
FIG. 2D is a detailed depiction of a section view of the helical windings of the deflectable tip.
Figure 2E:
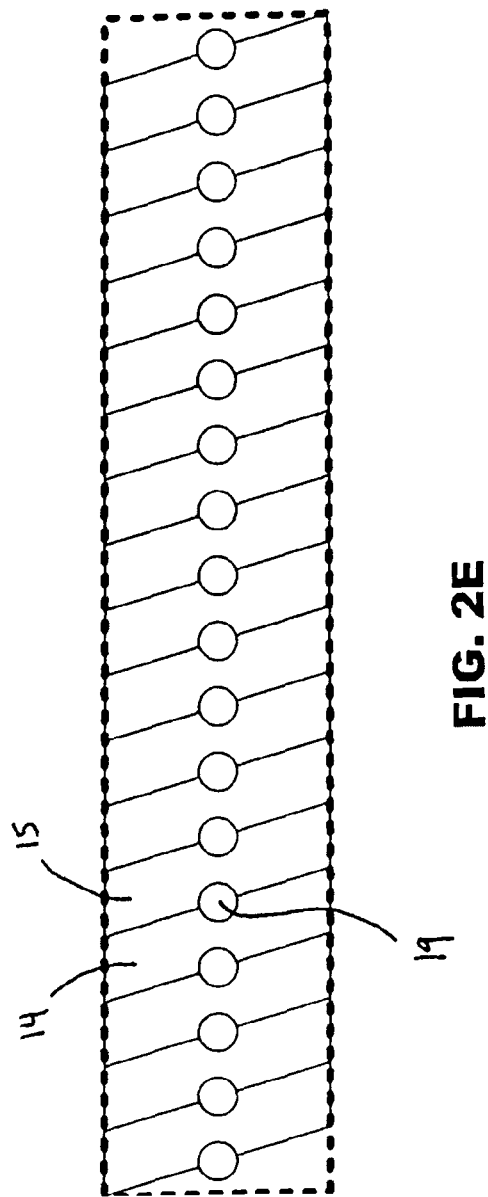
FIG. 2E shows the connections on every turn between the helical windings of the deflectable tip.
Figure 2F:
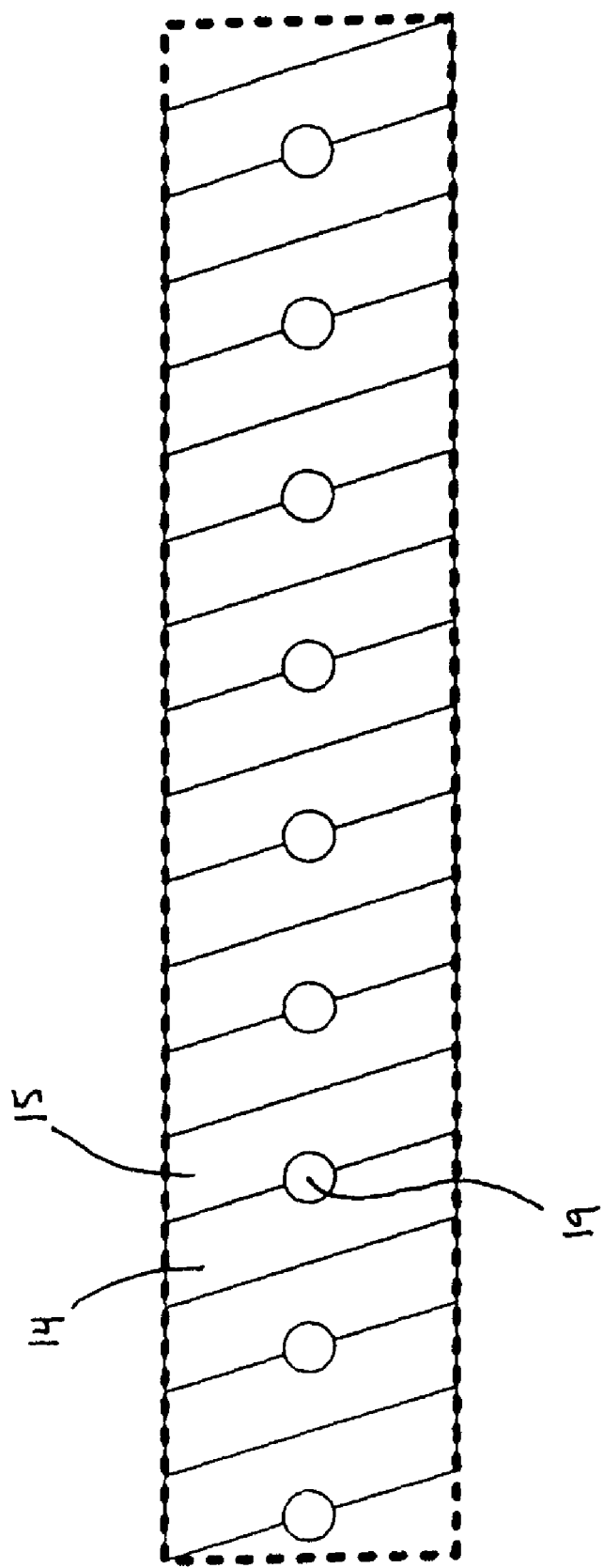
FIG. 2F shows the connections on every second turn between the helical windings of the deflectable tip.

This arrangement of two coils wound to two different diameters is more clearly shown in FIG. 2D. The individual turns of the coils are aligned with each other on one side of the nested structure (top of FIG. 2D), and an annular gap is present on the opposite side of the nested structure (bottom of FIG. 2D, and numeral 18 in FIG. 2A). Control wire 12 sits in this gap. On the side where the coil turns are aligned (top of FIG. 2D) as shown in FIG. 2E, a series of welds 19 may be used to maintain the alignment of coils 14 and 15. FIG. 2E shows the nested coil structure from the top and FIG. 2D shows a cross-sectional view of the coil structure. As shown in FIG. 2E, every abutment is welded, with conventional means such as laser welding. Alternatively, various weld patterns could be employed, for example, welding every second or third (and so on) abutment. In another embodiment, all abutments except every third, fourth, etc. could be welded. These variations yield an articulation structure with varying degrees of lateral flexibility, torqueability, and/or resilience (ability of articulation structure to re-straighten upon release of the control wire). In a preferred embodiment for coronary-type applications, every second abutment is welded (see FIG. 2F) This structure provides a deflectable tip that nearly fully re-straightens after the control wire is released.

With reference again to FIG. 2, an atraumatic polymer tip cap 13 may be used to encapsulate the distal-most portion of the deflectable tip region. Cap 13 may be insert molded on the end of the coil structure, or may be a heat-formed tube shrunk around the end of the coil structure. A preferred material is Pebax 5533.

Additionally, as illustrated in FIG. 2, the articulation structure may be covered by tip sheath 17. This sheath is preferably a thin walled tube of a flexible material such as Pebax or polyurethane, which may be heat-shrunk around the coil structure 14 and 15 or solvent-swelled and loaded onto the coil structure. A preferred material is Pebax 2533 or 3533. This sheath may be positioned on the coil structure 14 and 15 prior to or following formation of polymer tip cap 13. Tip sheath 1 serves to smoothen the surface of the coil structure, as well as imparting mechanical integrity and torsional stability, particularly if some of the abutments in the coil structure are left unwelded.

FIG. 3 illustrates a first embodiment of distal shaft region 21 of catheter 10. Guidewire tube 23 and control wire tube 29 abut the coil structure 14 and 15. Guidewire tube 23 may be an extruded tube of a lubricious polymer, such as high-density polyethylene. Control wire tube 29 may be formed from a lubricious polymer such as PTFE. Alternatively, the lumen for the control wire could be formed in the wall of the guidewire tube by fabricating the guidewire tube as a dual lumen extrusion of a lubricious material such as PTFE or HDPE. Control wire tube 29 may be ovalized to minimize diametric profile. A relatively short mechanical joining sleeve 38 may overlap guidewire tube 23, control wire tube 29, and coil structure 14 to mechanically connect them for subsequent processing. This tube is preferably heat formed to encapsulate the proximal end of the coil structure 14 and 15. The inner layer extension 37 surrounds the guidewire and control wire tubes 23 and 29 and extends distally to overlap the proximal end of the coil structure 14 and 15. The inner layer extension 37 is preferably annealed by heating (to prevent unwinding) before the coil is removed from the winding mandrel. Distal outer jacket 22 is then applied over the inner layer extension 37, extending somewhat distally as shown. The distal outer jacket 22 is preferably formed from a relatively flexible polymer such as Pebax, polyurethane, or polyethylene.

Distal outer jacket 22 may be formed from a thermoplastic tube (such as Pebax, polyurethane, or polyethylene), which is in turn heat shrunk around and into the inner layer extension with the aid of a separate length of heat-shrink tube (such as PTFE or FEP heat-shrink tubing). This heat-shrinking process forces distal outer jacket 22 to flow inside the inner layer extension 37 to make sealing contact with the outer surface of guidewire tube 23. As shown in FIG. 3, distal outer jacket 22 preferably includes inner layer 28 and outer layer 27, all formed together during the heat shrink process described above. The inner layer is preferably low density polyethylene, which encapsulates inner layer extension 37 and control wire tube 29, and makes intimate contact with guidewire tube 23, as seen in the cross section in FIG. 3A. As such, during use, blood is prevented from entering gap space 33 residing proximally between the torque shaft and outer jacket 32 (see FIG. 4). The outer layer 27 is preferably of a similar material as proximal outer jacket 32, such as Pebax, which yields a smooth surface amenable to an optional lubricious hydrophilic coating.

The main shaft region (shown enlarged in FIGS. 4 and 4A) includes outer jacket 32, preferably of a relatively flexible and lubricious polymer such as Pebax, Nylon, polyurethane, polyethylene, PTFE, or the like. Inside the outer jacket is a torque shaft, which serves to carry torque applied to handle 61 to deflectable tip 11, thus causing rotation of the tip when the handle is rotated. Between the torque shaft and the outer jacket, an optional gap 33 is illustrated. Gap 33 allows for localized relative rotation between the torque shaft and outer jacket 32. This minimizes frictional counter-torque directly on the torque shaft in regions of the vascular system where high frictional surfaces may be encountered, such as areas of calcification. Alternatively, gap 33 may be eliminated to reduce shaft profile. In this case, the outer jacket may be in "line-to-line" contact with the outer surface of the torque shaft. This may be accomplished, for example, by utilizing a heat shrinkable tubing for the outer jacket, or applying a polymeric coating such as a UV-curable polyurethane.

The torque shaft may be fabricated as a multi-filar, multi-layer wound coil structure. In one embodiment, shown in FIG. 4, the torque shaft comprises inner winding 34, intermediate winding 35, and outer winding 36. Each layer is wound with the opposite "lay" of the previous layer, thus imparting bi-directional torsional rigidity to the structure, while allowing for significant flexibility. The inner most layer 34 may be wound on an annealed winding mandrel, which is removable by longitudinal stretching, which necks the diameter of the mandrel away from the inner layer of the drive shaft.

In one embodiment, each layer may be formed from four adjacent filars or wires. In order to minimize "backlash," each layer may be wound directly on the previous layer with the wires under tension. This prevents any radial gaps between adjacent layers. The residual tension of each layer may be maintained either by securing the layer to the winding mandrel by mechanical means such as a clamp, solder, or adhesive before severing the wires and starting the next layer. Alternatively, the subsequent layer may be wound directly on top of the previous layer without terminating the wires. Once the third layer is wound, the ends may be temporarily secured to the layer beneath by solder or adhesive. This prevents any layers of the torque shaft from subsequently unwinding. The winding mandrel may then be stretched and removed from the inside of the torque shaft.

With regard to the degree of tensioning on the wires during winding, it may be preferable, particularly for portions of the torque shaft that will encounter tortuosity (such as the distal portion of the catheter in a coronary type application), to apply just enough tension to eliminate "backlash." This serves to minimize internal binding between the coil layers when the shaft is curved. Excess tension during winding can increase the straight torsional stiffness of the torque shaft, but when such a shaft encounters bending, the internal binding that results from the excess tension can require higher torque to be applied to the shaft in order to cause it to rotate within that curved path. A preferred torque shaft has the proximal region wound with higher tension of the individual wires, and lower tension on the distal region.

FIG. 4B shows the junction 31 between the main shaft region 41 and the distal shaft region 21. The inner layer 34 of the torque shaft extends distally beyond the outer two layers 35 and 36. To fabricate this inner layer extension, the distal-most portion of the inner layer of the drive shaft may be wound first on the winding mandrel. Once at the proximal end, this layer may be reversed back to form the second layer, with an opposite "lay." The second layer may be wound until a point short of (proximal) to the starting point of the first layer, and then may be reversed back to form the third layer. To prevent the inner layer extension from "springing" out after the winding mandrel is removed, inner layer extension 37 may be annealed by conventional methods.

The distal shaft region 21 also may include distal outer jacket 22. The distal outer jacket serves to impart some torsional stability and strength to inner layer extension 37. The inner layer extension on its own has relatively low torsional strength, because it is a single layer. Distal outer jacket 22 serves to prevent expansion due to twisting from applied torque, thereby increasing its torsional rigidity in at least one direction. To improve torsional rigidity in the opposite direction, distal outer jacket 22 may be further entrained in the inner layer extension by preferably heat-forming the jacket material into the windings of coil 37. This can be accomplished by means of applying a suitable heat-shrinkable tubing to the outside of the distal outer jacket and forming the jacket tube to a smaller outer diameter and squeezing material into the coil. Distal outer jacket 22 may be secured to proximal outer jacket 32 by thermal or adhesive bonding. Alternatively, distal outer jacket 22 may be an integral extension of proximal outer jacket 32, wherein the distal portion may be shrunk down to inner layer extension coil 37 by heat forming, or the use of heat-shrinkable tubing for outer jacket 32. Preferably, however, distal outer jacket 22 is a separate tubing component secured to proximal outer jacket 32. This facilitates the use of a more flexible polymeric material for the distal outer jacket, such as a lower durometer Pebax or polyurethane, versus a higher durometer material for the proximal outer jacket.

The distal shaft region 21 in FIG. 1 is of a lower profile than the main shaft region 41, since it has only a single layer of the torque shaft, however it is not as torsionally rigid as the main shaft region. In a coronary-type application, the distal shaft region is preferably about 1.5-4 cm long and most preferably about 3 cm long. In use, this length allows for the lower profile distal shaft region 21 to traverse most lesions, placing distal guidewire opening 9 (see FIG. 2) distal of the lesion. The guidewire (not shown) can then be readily exchanged, if desired. For example, a relatively stiff guidewire may be used to penetrate the lesion (as described in U.S. application Ser. No. 10/301,779, filed Nov. 22, 2002, incorporated herein by reference in its entirety), then the distal shaft region of the catheter is passed through the lesion, while maintaining position of the guidewire. Then the stiff guidewire is exchanged for a more floppy-tipped guidewire, which is more appropriate for deep placement in the coronary vasculature. And although the distal shaft region is less torsionally rigid than the main shaft region, if it is relatively short, the loss in the catheter's overall torsional stiffness is relatively minor.

Figure 7A:
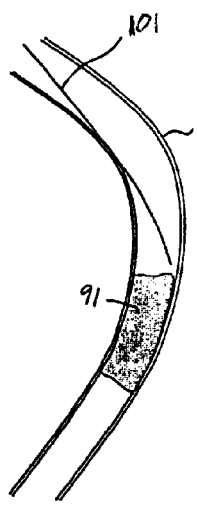
FIGS. 7A-7C are cross section views of an occluded vessel showing a guidewire crossing the occlusion through use of the catheter of FIGS. 1 and 5, according to one embodiment of the present invention.
Figure 7B:
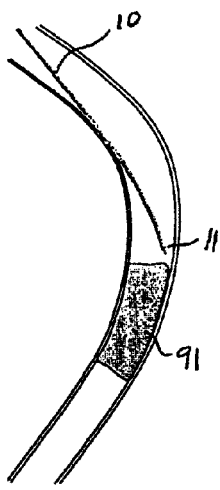
Figure 7C:
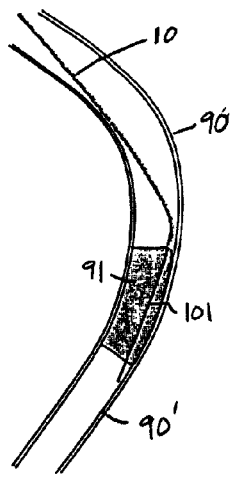
Figure 7D:
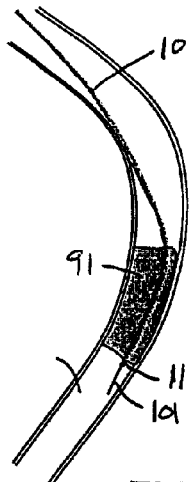
FIG. 7D is a cross section view of an occluded vessel showing a guidewire and the catheter of FIGS. 1 and 5 crossing the occlusion, according to one embodiment of the present invention.
Figure 7E:
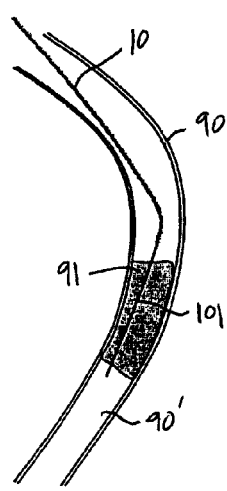
FIG. 7E is a cross section view of an occluded vessel showing a guidewire centered and crossing the occlusion through use of the catheter of FIGS. 1 and 5, according to another embodiment of the present invention.
Figure 7F:
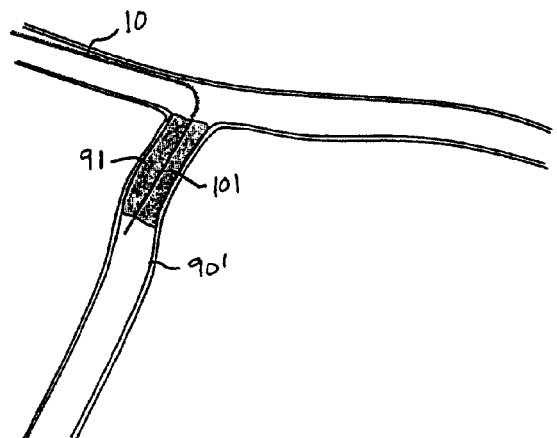
FIG. 7F is a cross section view of an occlusion near a bifurcation showing a guidewire crossing the occlusion through use of the catheter of FIGS. 1 and 5, according to another embodiment of the present invention.

In use, the physician provides catheter 10 having elongate tubular member 41 with a proximal end and a distal end, and deflectable tip 11 at the distal end of catheter 10 as described above. This may be done after the physician has been unable to cross the lesion with guidewire 101 as shown in FIG. 7A. The catheter 10 is advanced to a region of interest in artery 90 proximal lesion 91 as shown in FIG. 7B. The control wire is operated to direct deflectable tip 11 toward lesion 91. Guidewire 101 is advanced through the lumen of catheter 10 and into lesion 91 to cross the lesion as shown in FIG. 7C. For a short lesion, the guidewire may be advanced in a single pass. For a longer lesion, as shown in FIG. 7D, the guidewire is advanced in small increments, and catheter 10 is advanced into lesion 91 so that catheter 10 can guide further advancement of guidewire 101. In FIG. 7E, catheter 10 has been pulled back from lesion 91 to create a path for guidewire 101 that is both parallel and centered within the lumen of vessel 90. FIG. 7F shows the use of catheter 10 in crossing occlusion 91 near a bifurcation. The same steps as discussed above and in U.S. application Ser. No. 10/301,779, filed Nov. 22, 2002, incorporated herein by reference in its entirety, can be used with the present invention.

Once the lesion has been accessed in this manner, a dilatation balloon can be used to dilate the lesion. In one embodiment, the catheter of the present invention carries the dilatation balloon, as described below with reference to FIGS. 5 and 5A. The catheter is advanced over the guidewire to cross the lesion and the balloon is expanded to dilate the lesion. In another embodiment, the catheter is then removed from the region of interest while the guidewire is maintained across the lesion. An angioplasty catheter is then advanced across the lesion, and the lesion is dilated. In a further alternative embodiment, the catheter is removed from the region of interest while the guidewire is maintained across the lesion. A stent catheter is then advanced across the lesion, and the lesion is dilated with a stent.

Figure 5:
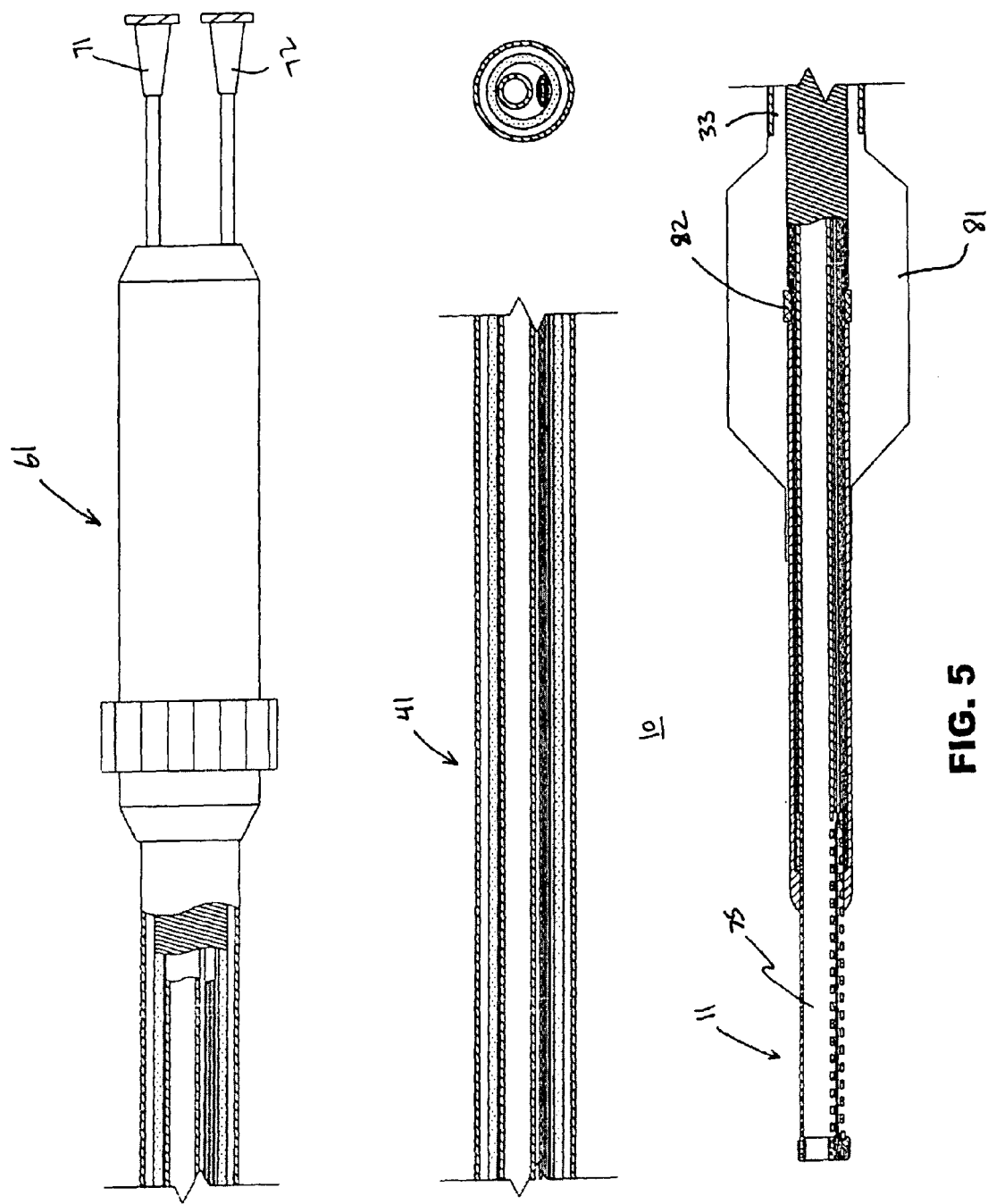
FIG. 5 depicts a partial section view of a balloon dilatation catheter according to the present invention.

FIGS. 5 and 5A illustrate an alternative embodiment wherein catheter 10 includes a dilation balloon (shown in its expanded state). Dilation balloon 81 is used to facilitate pre-dilation of the lesion, once a guidewire has successfully been placed across the lesion. The inclusion of a pre-dilation balloon eliminates the need for a placement and use of a separate balloon dilation catheter specifically for this use. Pre-dilation is usually performed prior to the placement of a stent in a total occlusion.

In this embodiment of the catheter, components with like numbers are the same as components described above. Dilation balloon 81 is mounted near the distal end of the catheter, preferably straddling region 31 where the torque shaft transitions from multi-layer to the single-layer inner layer extension. Radiopaque marker 82 is secured to the torque shaft at this transition. The balloon includes proximal and distal waist segments, numerals 83 and 84, respectively. The distal segment 84 is attached to distal outer jacket 22 by suitable means such as heat bonding or adhesive (not shown). The proximal segment is attached to outer jacket 32, again by similar suitable means.

To facilitate inflation and deflation of balloon 81, outer jacket 32 is sized to allow for annular gap 33 between the outer jacket and the torque shaft to be large enough to carry inflation fluid to and from balloon 81. For a coronary-type application, a balloon may be approximately 1.5 to 2.5 mm in diameter when expanded, and more preferably approximately 2 mm, and approximately 10 to 25 mm in length, and more preferably approximately 20 mm in length. To accommodate these balloon dimensions, the inflation lumen is approximately 0.001 to 0.004 inch in gap width, and more preferably approximately 0.002 inch wide. The annular gap, or inflation lumen, communicates at a proximal end with luer 72.

The balloon is preferably fabricated of a material that can withstand high pressures, on the order of approximately 10 to 20 atmospheres. Such a balloon may be fabricated from blow-molding a tubing of polyethylene teraphthalate, polyamide, PEBAX, PTFE, Arnitel, or other high strength materials.

In use, the balloon affixed in the position described above allows for the catheter to direct and support the guidewire crossing of the lesion, followed with crossing of the lesion with the lower profile distal shaft region (where confirmation of whether the guidewire tip is in the "true lumen" may be performed, as described in as described in U.S. application Ser. No. 10/301,779, filed Nov. 22, 2002, incorporated herein by reference in its entirety). Then, the deflated balloon is passed across the lesion to dilate, or pre-dilate the lesion.

The balloon catheter above could also be fashioned as a stent delivery catheter. Additionally, other diagnostic/treatment modalities could be integrated into the basic design of the deflectable tip catheter, including any one or more of contrast delivery, device delivery, ultrasound, atherectomy, laser, fluid or mechanical thrombectomy, and localized drug delivery.

Figure 6:
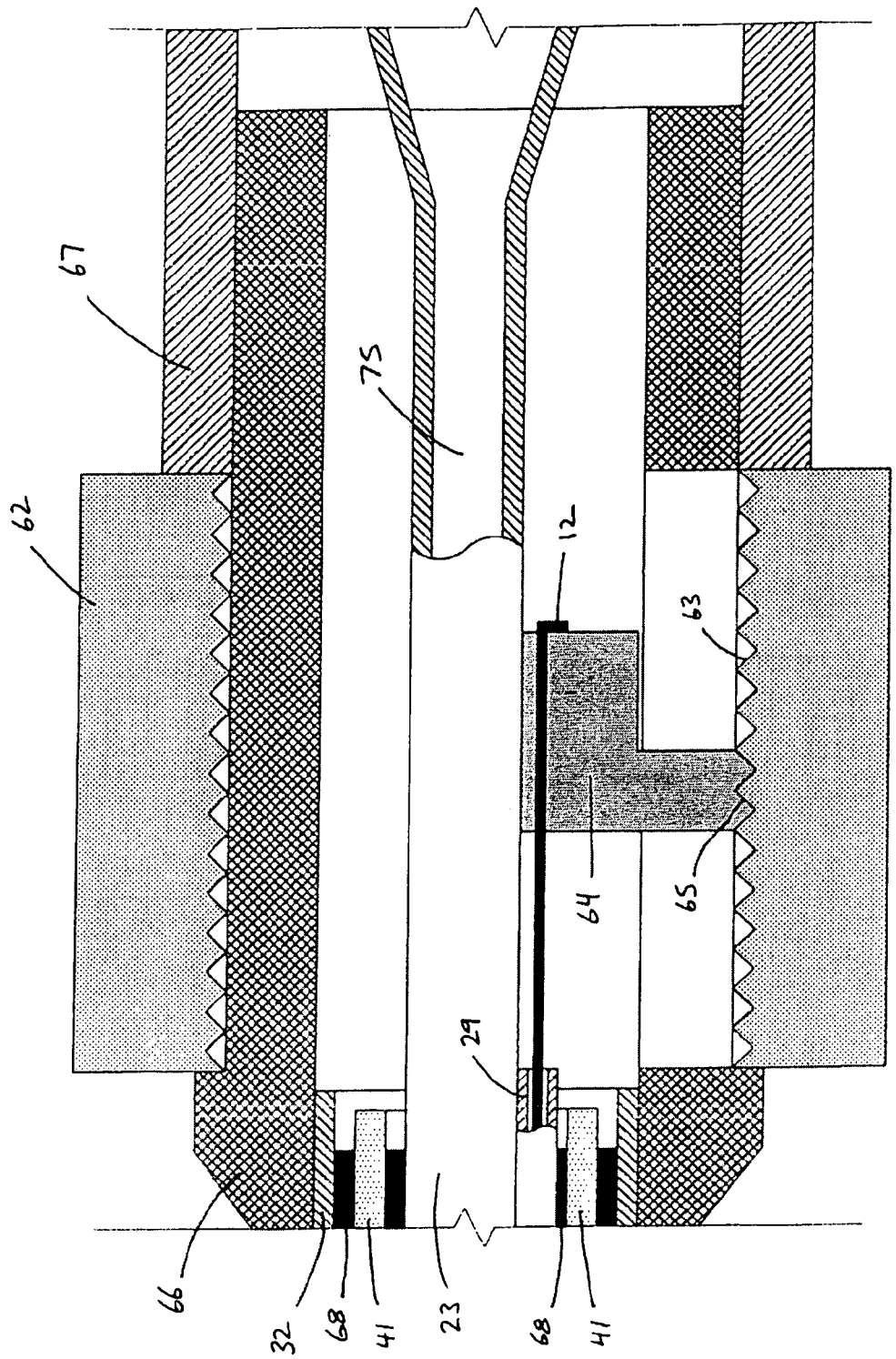
FIG. 6 depicts a portion of the handle of the catheter of FIGS. 1 and 5.

FIG. 6 is an expanded view of a portion of one embodiment of handle 61 of FIG. 1, for the non-balloon version of catheter 10. The handle is comprised of 2 portions, tubular distal body portion 66 secured concentrically in tubular proximal body portion 67. Knob 62 is positioned in the recessed area of body 66, and is free to rotate relative to the body. The proximal end of outer jacket 32 is secured to the distal body portion by suitable means, such as adhesive 68. To transmit torque and rotation of the handle to the torque shaft 41, the proximal end of the outer jacket 32 is also secured to the proximal end of the torque shaft 41, by suitable means such as heat bonding or adhesive (shown). It is also preferable to secure the proximal end of torque shaft 41 to guidewire tube 23 and control wire tube 29, so that rotation of the handle rotates all of the components of the catheter at their proximal ends. This securement is done by suitable means such as adhesive.

While not shown in the figure, it is desirable to not completely seal off the lumen between outer jacket 32 and the torque shaft (gap 33 of FIG. 4). Complete sealing would render that space difficult to sterilize, particularly with ethylene oxide gas sterilization. To provide a vent to this space, one or more small sections of tubing (e.g. polyimide tubing) are placed within the heat bond between the outer jacket and the drive shaft, and/or within the adhesive bond between the drive shaft and the guidewire tube. This same venting approach is also useful in a handle for a device which includes a dilation balloon, as this provides access between the interior of the handle and the inflation lumen.

Slider 64 is configured to move axially relative to the body, to move control wire 12 relative to control wire tube 29. The slider has a projection which passes through a slot opening in the side of the distal body portion. The interior of knob 62 is helically threaded to engage the projection of slider 64, which has corresponding threads 65 on its outer aspect. Control wire 12 is secured to the slider. Relative rotation of knob 62 with handle 61 causes slider 64 to move axially, thus moving control wire 12 and actuating deflectable tip 11 (see FIG. 2C). The tip can be re-straightened by moving slider 64 back in a distal direction (see FIG. 2B).

Although particularly described for coronary-type applications, the devices of the present invention are also useful in other applications, including but not limited to carotid arteries, cerebral arteries, other peripheral arteries, renal arteries, veins, and other body lumens wherein placement of guidewires or other devices is performed.

The catheters of preferred embodiments in accordance with the devices described herein for coronary type applications will typically have a length between approximately 100-160 cm, preferably approximately 120-140 cm. The diameter of the outer jacket will typically be approximately 0.040×0.048 in. The gap between the outer jacket and the torque cable will typically be approximately 0.0005 to 0.0015 in. on each side of the torque cable, more preferably approximately 0.001 in. The torque cable may be formed from filars or wires of heavily cold-worked 304 stainless steel ribbon, 0.0015×0.008 in. The coils are typically formed from ribbon. The inner coil (of the articulation structure) is preferably wound to an inner diameter of approximately 0.016 in. to accommodate a typical 0.014 in. coronary guidewire, using a ribbon of approximately 0.002×0.005 in. The control wire is typically formed of a ribbon of stainless steel approximately 0.001×0.005 in. The outer coil is typically wound to leave a gap for the control wire of approximately 0.002 in. using a ribbon of approximately 0.002 in. thick by approximately 0.006 to 0.010 in. wide. To facilitate radiopacity, one or both coils 14 and 15 in FIG. 2 may be formed of radiopaque material such as platinum alloy. Preferably, the inner coil is of platinum alloy, while the outer coil is of a cold-worked 304 stainless steel.

For a coronary-type application, a preferred articulation structure has an articulable length of about 1 to 6 mm, and more preferably about 3 to 4 mm. A further alternative is to fabricate the outer layer 27 of the distal outer jacket 22 of multiple longitudinally arranged tubes of varying stiffness. For example, the distal outer layer 27 could be fabricated of 25 durometer Pebax, and the proximal outer layer 32 could be fabricated of 35 durometer Pebax. This creates a distal outer jacket which progresses in the proximal direction from higher to lower flexibility, which aids in the trackability of the catheter. The foregoing ranges and materials are set forth solely for the purpose of illustrating typical device dimensions and materials and would vary, depending on the particular clinical application. For example, catheter lengths might be shorter for peripheral artery applications, and longer for neurovascular (e.g., carotid) applications. The actual dimensions and materials of a device constructed according to the principles of the present invention may obviously vary outside of the listed ranges and materials without departing from those basic principles.

Although the foregoing invention has, for the purposes of clarity and understanding, been described in some detail by way of illustration and example, it will be understood that certain changes and modifications may be practiced which will still fall within the scope of the appended claims. It will moreover be understood that any feature or features from any drawing, embodiment, or method can be combined with the features from any other drawing, embodiment, or method, including those incorporated by reference herein.

What is claimed is:

1. A catheter, comprising:
    an elongate tubular member having a proximal region, a distal region, and a lumen extending therebetween;
    a multilayer torque cable in the proximal region of the elongate tubular member, the multilayer torque cable having a first helical coil and a second helical coil, the first helical coil nested within the second helical coil and wound in a reverse direction from the second helical coil so that rotation of the first helical coil in a first direction causes the first helical coil to expand while rotation of the second helical coil in the first direction causes the second helical coil to compress and thereby interfere with the expansion of the first helical coil;
    a monolayer helical coil in the distal region of the elongate tubular member, wherein the monolayer helical coil is an extension of the first helical coil; and
    an outer jacket surrounding the monolayer helical coil to restrict expansion on rotation of the monolayer helical coil.

2. The catheter of claim 1, wherein the multilayer torque cable further comprises a third helical coil surrounding the second helical coil.

3. The catheter of claim 1, wherein the monolayer helical coil is annealed to prevent unwinding expansion on torquing the catheter.

4. The catheter of claim 1, wherein the first helical coil is multifilar.

5. The catheter of claim 1, wherein the second helical coil is multifilar.

6. The catheter of claim 1, wherein the monolayer helical coil is multifilar.

7. The catheter of claim 1, further comprising a balloon mounted on the distal region of the elongate tubular member, the balloon defining a chamber that communicates with an inflation lumen that extends to the proximal region of the elongate tubular member.

8. The catheter of claim 7, wherein a second outer jacket is disposed about the multilayer torque cable, and wherein a proximal end of the balloon is bonded to the second outer jacket and a distal end of the balloon is bonded to the outer jacket surrounding the monolayer helical coil.

* * * * *